US012625214B2

(12) United States Patent
Xiao et al.

(10) Patent No.: US 12,625,214 B2
(45) Date of Patent: May 12, 2026

(54) ULTRA-LOW FIELD MAGNETIC RESONANCE IMAGING SYSTEM AND METHOD THEREOF

(71) Applicant: HANGZHOU WEIYING MEDICAL TECHNOLOGY CO., LTD., Hangzhou (CN)

(72) Inventors: Linfang Xiao, Hangzhou (CN); Ruixing Zhu, Hangzhou (CN)

(73) Assignee: HANGZHOU WEIYING MEDICAL TECHNOLOGY CO., LTD., Hangzhou (CN)

( * ) Notice: Subject to any disclaimer, the term of this patent is extended or adjusted under 35 U.S.C. 154(b) by 216 days.

(21) Appl. No.: 18/646,828

(22) Filed: Apr. 26, 2024

(65) Prior Publication Data

US 2025/0076437 A1      Mar. 6, 2025

(30) Foreign Application Priority Data

Aug. 29, 2023    (CN) .......................... 202311098681.5

(51) Int. Cl.
| | |
|---|---|
| *G01R 33/56* | (2006.01) |
| *A61B 5/055* | (2006.01) |
| *G01R 33/48* | (2006.01) |
| *G01R 33/50* | (2006.01) |
| *G01R 33/561* | (2006.01) |

(52) U.S. Cl.
CPC .......... *G01R 33/5608* (2013.01); *A61B 5/055* (2013.01); *G01R 33/4818* (2013.01); *G01R 33/50* (2013.01); *G01R 33/561* (2013.01)

(58) Field of Classification Search
CPC ....................... G01R 33/5608; G01R 33/4818; G01R 33/50; G01R 33/561; G01R 33/445; A61B 5/055; Y02A 90/30; G06N 3/0464; G06N 3/048; G06N 3/08; G06T 17/00; G06T 2207/10136; G06T 2207/20081; G06T 2207/20084
See application file for complete search history.

(56) References Cited

U.S. PATENT DOCUMENTS

2020/0034998 A1*    1/2020    Schlemper ......... G01R 33/5608
* cited by examiner

*Primary Examiner* — G.M. A. Hyder

(57) ABSTRACT

An ultra-low field magnetic resonance imaging system and a method thereof are provided. The ultra-low field magnetic resonance imaging system includes means for collecting a down-sampled three-dimensional ultra-low field magnetic resonance data; means for processing a three-dimensional ultra-low field magnetic resonance data to obtain a three-dimensional isotropic ultra-low field magnetic resonance image; and means for processing data, for inputting the three-dimensional isotropic ultra-low field magnetic resonance image into a pre-trained image enhancement model to obtain a full-sampled three-dimensional magnetic resonance enhanced image.

10 Claims, 6 Drawing Sheets

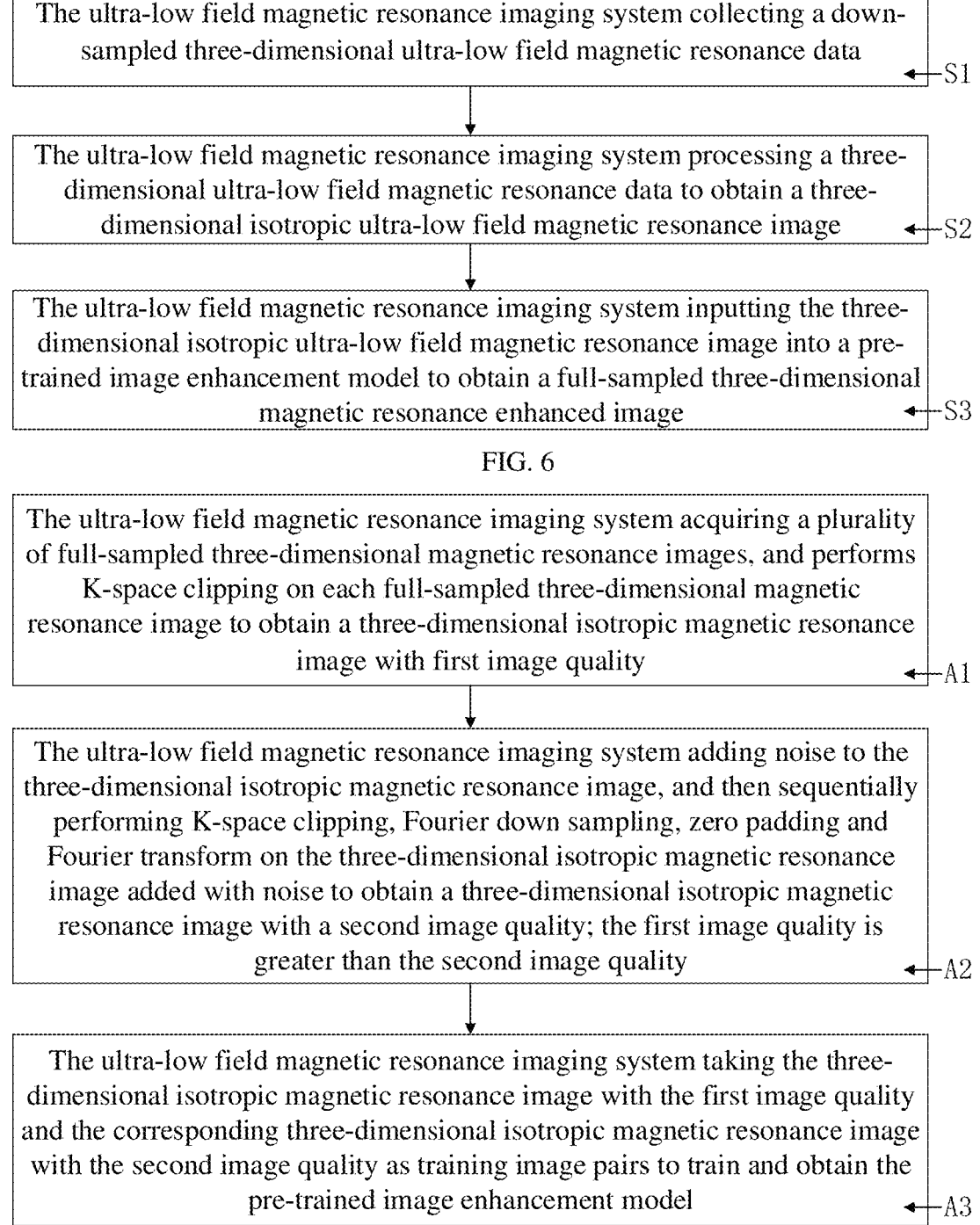

The ultra-low field magnetic resonance imaging system collecting a down-sampled three-dimensional ultra-low field magnetic resonance data   ◄─S1

The ultra-low field magnetic resonance imaging system processing a three-dimensional ultra-low field magnetic resonance data to obtain a three-dimensional isotropic ultra-low field magnetic resonance image   ◄─S2

The ultra-low field magnetic resonance imaging system inputting the three-dimensional isotropic ultra-low field magnetic resonance image into a pre-trained image enhancement model to obtain a full-sampled three-dimensional magnetic resonance enhanced image   ◄─S3

FIG. 6

The ultra-low field magnetic resonance imaging system acquiring a plurality of full-sampled three-dimensional magnetic resonance images, and performs K-space clipping on each full-sampled three-dimensional magnetic resonance image to obtain a three-dimensional isotropic magnetic resonance image with first image quality   ◄─A1

The ultra-low field magnetic resonance imaging system adding noise to the three-dimensional isotropic magnetic resonance image, and then sequentially performing K-space clipping, Fourier down sampling, zero padding and Fourier transform on the three-dimensional isotropic magnetic resonance image added with noise to obtain a three-dimensional isotropic magnetic resonance image with a second image quality; the first image quality is greater than the second image quality   ◄─A2

The ultra-low field magnetic resonance imaging system taking the three-dimensional isotropic magnetic resonance image with the first image quality and the corresponding three-dimensional isotropic magnetic resonance image with the second image quality as training image pairs to train and obtain the pre-trained image enhancement model   ◄─A3

ULTRA-LOW FIELD MAGNETIC RESONANCE IMAGING SYSTEM AND METHOD THEREOF

CROSS-REFERENCE TO RELATED APPLICATIONS

This application claims priority to Chinese patent application No. 202311098681.5, filed on Aug. 29, 2023, and titled "RAPID ULTRA-LOW FIELD MAGNETIC RESONANCE IMAGING SYSTEM AND METHOD THEREOF". The content of the above identified application is hereby incorporated by reference in its entirety.

TECHNICAL FIELD

The present disclosure relates to the field of magnetic resonance imaging technology, and in particular, to an ultra-low field magnetic resonance imaging system and a method thereof.

BACKGROUND

Ultra-low field magnetic resonance imaging technology has many advantages over magnetic resonance imaging approaches, including excellent openness, ultra-quiet operation, no requirement for electromagnetic shielding, miniaturization, lightweight portability, and the ability to be positioned bedside for patient convenience. It provides a low-cost, low-power, patient-centered solution for clinical magnetic resonance examination, and a tool for specialist diagnosis and general diagnosis non-imaging departments. However, ultra-low field magnetic resonance signals are weak and susceptible to noise interference, resulting in diminished imaging quality and low image resolution.

At present, methods to enhance an image quality of the ultra-low field magnetic resonance mainly include a multiple averaging method, an interpolation method, an image reconstruction algorithm, and so on. Although the multiple averaging method does enhance the image quality to a certain extent, it takes a lot of time, consumes significant resources and is costly. In addition, an image obtained by the multiple averaging method lacks details, clarity, and accuracy. Although time cost of the interpolation method is low, its capability to enhance image quality is limited and effect is inconsistent. Relying solely on the conventional image reconstruction algorithms, the image quality of ultra-low field magnetic resonance imaging still exhibits shortcomings in spatial resolution, signal-to-noise ratio, and artifact level. These limitations stem from the fundamental principle of magnetic resonance signal generation, that is, an intensity of magnetic resonance signal is proportional to the square of the main magnetic field strength. Moreover, a typical MRI (magnetic resonance imaging) resolution can be anisotropic, and clinical MRI scans often require imaging in multiple directions, leading to extended scanning time. Prolonged scanning time leads to motion artifacts, which degrades the image quality. Subpar image quality will result in unsatisfactory diagnostic results, significantly impeding a widespread application of ultra-low field magnetic resonance in clinical practice.

SUMMARY

According to various embodiments, the present disclosure provides an ultra-low field magnetic resonance imaging system, including means for collecting a down-sampled three-dimensional ultra-low field magnetic resonance data; means for processing the three-dimensional ultra-low field magnetic resonance data to obtain a three-dimensional isotropic ultra-low field magnetic resonance image; and means for inputting the three-dimensional isotropic ultra-low field magnetic resonance image into a pre-trained image enhancement model to obtain a full-sampled three-dimensional magnetic resonance enhanced image.

In some embodiments, the down-sampled three-dimensional ultra-low field magnetic resonance data includes K-space data with Fourier down sampling along two dimensions. T1-weighted magnetic resonance data is collected by inversion recovery fast spin echo sequence, and T2-weighted magnetic resonance data is collected by fast spin echo sequence.

In some embodiments, processing the three-dimensional ultra-low field magnetic resonance data includes performing zero-padding and Fourier transform on the three-dimensional ultra-low field magnetic resonance data to obtain the three-dimensional isotropic ultra-low field magnetic resonance image.

In some embodiments, the ultra-low field magnetic resonance imaging system further includes means for acquiring a plurality of full-sampled three-dimensional magnetic resonance images, and performing K-space clipping on each of the full-sampled three-dimensional magnetic resonance enhanced image to obtain a three-dimensional isotropic magnetic resonance image with first image quality;

means for adding noise to the three-dimensional isotropic magnetic resonance image, and then sequentially performing K-space clipping, Fourier down sampling, zero-padding, and Fourier transform on the three-dimensional isotropic magnetic resonance image added with the noise to obtain a three-dimensional isotropic magnetic resonance image with second image quality; the first image quality is greater than the second image quality; and means for taking the three-dimensional isotropic magnetic resonance image with the first image quality and the corresponding three-dimensional isotropic magnetic resonance image with the second image quality as a training image pair to train and obtain the pre-trained image enhancement model.

In some embodiments, a network structure of the image pre-trained enhancement model includes a first convolution component, a multi-scale feature extraction component, a spatial attention component, a second convolution component, a first channel attention convolution component, a sub-pixel convolution component, and a first convolution layer. An input of the first convolution component is an input of the image enhancement model, and an output of the first convolution component is connected to an input of the multi-scale feature extraction component; an input of the spatial attention component is connected to an output of the multi-scale feature extraction component, and an output of the spatial attention component is connected to an input of the second convolution component; an input of the first channel attention convolution component is connected to an output of the second convolution component, and an output of the first channel attention convolution component is connected to an input of the sub-pixel convolution component; and an input of the first convolution layer is connected to an output of the sub-pixel convolution component, and voxel intensity of the input of the image enhancement model after up-sampling and voxel intensity of an output of the first convolution layer are added to serve as an output of the image enhancement model.

In some embodiments, the multi-scale feature extraction component includes a first stride convolution component, a second channel attention convolution component, a third channel attention convolution component, a fourth channel attention convolution component, a first up-sampling layer, a first residual channel attention component, a second up-sampling layer, a second residual channel attention component, and a second stride convolution component. An input of the first stride convolution component is connected to the output of the first convolution component, and an output of the first stride convolution component is connected to an input of the second channel attention convolution component; an input of the third channel attention convolution component is connected to an output of the second channel attention convolution component, and an output of the third channel attention convolution component is connected to an input of the fourth channel attention convolution component; an input of the first up-sampling layer is connected to an output of the fourth channel attention convolution component, and an output of the first up-sampling layer and the output of the third channel attention convolution component are connected to an input of the first residual channel attention component after channel splicing; an input of the second up-sampling layer is connected to an output of the first residual channel attention component, and an output of the second up-sampling layer and the output of the second channel attention convolution component are connected to an input of the second residual channel attention component after channel splicing; and an input of the second stride convolution component is connected to an output of the second residual channel attention component, and an output of the second stride convolution component is connected to the input of the spatial attention component.

In some embodiments, the first channel attention convolution component, the second channel attention convolution component, the third channel attention convolution component, and the fourth channel attention convolution component all include a third residual channel attention component, a strided convolution layer, and a linear rectification function with leakage which are connected in sequence.

In some embodiments, the first residual channel attention component, the second residual channel attention component, and the third residual channel attention component all include a third convolution component, a second convolution layer, and a channel attention component connected in sequence, and voxel intensity of an input of the second convolution component and voxel intensity of an output of the channel attention component are added to serve as an output of the first residual channel attention component, an output of the second residual channel attention component, or an output of the third residual channel attention component.

The present disclosure further provides an ultra-low field magnetic resonance imaging method, which is applied to the above ultra-low field magnetic resonance imaging system, including:

step 1, the ultra-low field magnetic resonance imaging system collecting a down-sampled three-dimensional ultra-low field magnetic resonance data;

step 2, the ultra-low field magnetic resonance imaging system processing the three-dimensional ultra-low field magnetic resonance data to obtain a three-dimensional isotropic ultra-low field magnetic resonance image; and step 3, the ultra-low field magnetic resonance imaging system inputting the three-dimensional isotropic ultra-low field magnetic resonance image into a pre-trained image enhancement model to obtain a full-sampled three-dimensional magnetic resonance enhanced image.

In some embodiments, before step 1 is executed, the ultra-low field magnetic resonance imaging method further includes a model training process, and the model training process includes following steps:

step A1, the ultra-low field magnetic resonance imaging system acquiring a plurality of full-sampled three-dimensional magnetic resonance images, and performs K-space clipping on each full-sampled three-dimensional magnetic resonance image to obtain a three-dimensional isotropic magnetic resonance image with first image quality;

step A2, the ultra-low field magnetic resonance imaging system adding noise to the three-dimensional isotropic magnetic resonance image, and then sequentially performing K-space clipping, Fourier down sampling, zero padding and Fourier transform on the three-dimensional isotropic magnetic resonance image added with noise to obtain a three-dimensional isotropic magnetic resonance image with a second image quality; the first image quality is greater than the second image quality, and step A3, the ultra-low field magnetic resonance imaging system taking the three-dimensional isotropic magnetic resonance image with the first image quality and the corresponding three-dimensional isotropic magnetic resonance image with the second image quality as training image pairs to train and obtain the pre-trained image enhancement model.

The above technical scheme has the following advantages or beneficial effects:

1) a quality of ultra-low field magnetic resonance imaging is enhanced, including improving image signal-to-noise ratio, reducing image artifacts, and increasing image resolution; and 2) a scanning time of ultra-low field magnetic resonance imaging is reduced, enabling ultra-low field magnetic resonance imaging with great quality and rapid imaging.

BRIEF DESCRIPTION OF THE DRAWINGS

In order to more clearly illustrate the technical solutions in the embodiments of the present disclosure or the related technology, the accompanying drawings to be used in the description of the embodiments or the related technology will be briefly introduced below, and it will be obvious that the accompanying drawings in the following description are only some of the embodiments of the present disclosure, and that, for one skilled in the art, other accompanying drawings can be obtained based on these accompanying drawings without putting in creative labor.

FIG. 6 is a schematic flowchart of an ultra-low field magnetic resonance imaging method in one or more embodiments in the present disclosure.

FIG. 7 is a schematic flowchart of a model training process in one or more embodiments in the present disclosure.

DETAILED DESCRIPTION OF THE EMBODIMENT

The following describes the present disclosure in detail with reference to the accompanying drawings and specific embodiments. The present disclosure is not limited to this implementation manner, and other implementation manners may fall within the scope of the present disclosure as other implementation manners conform to the essence of this application.

Figure 1:
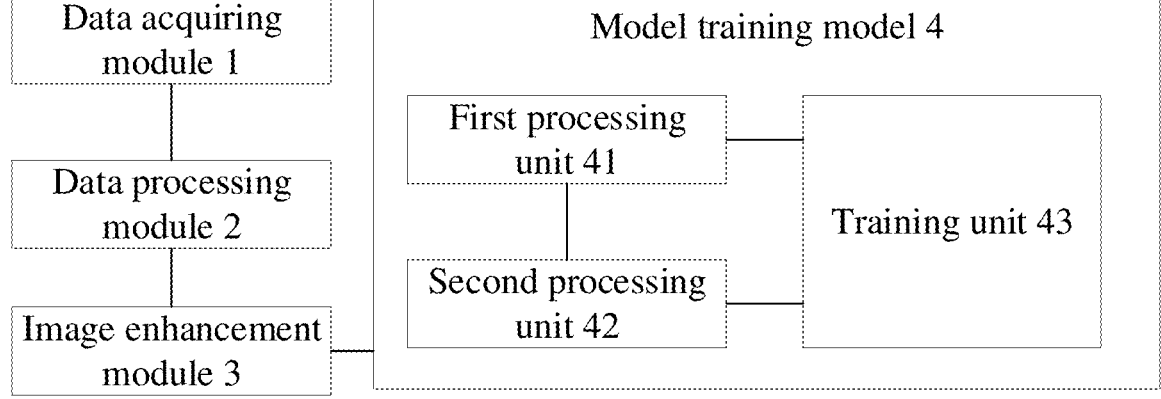
FIG. 1 is a schematic view of an ultra-low field magnetic resonance imaging system in one or more embodiments in the present disclosure.

Referring to FIG. 1, the present disclosure provides an ultra-low field magnetic resonance imaging system, including a data acquiring module 1, a data processing module 2, and an image enhancement module 3, the data acquiring module 1 is configured for acquiring a down-sampled three-dimensional ultra-low field magnetic resonance data;

the data processing module 2 is connected to the data acquisition module 1, and is configured for processing a three-dimensional ultra-low field magnetic resonance data to obtain a three-dimensional isotropic ultra-low field magnetic resonance image; and the image enhancement module 3 is connected to the data processing module 2, and is configured for inputting the three-dimensional isotropic ultra-low field magnetic resonance image into a pre-trained image enhancement model to obtain a full-sampled three-dimensional magnetic resonance enhanced image.

Specifically, in the embodiment, the above ultra-low field magnetic resonance imaging system can be an ultra-low field magnetic resonance system with a magnetic field strength of 0.055 T, the down-sampled three-dimensional ultra-low field magnetic resonance data may include K-space data with Fourier down sampling along two dimensions, and both down sampling rates along two phase encoding dimensions are 0.7. T1-weighted magnetic resonance data may be collected by inversion recovery fast spin echo (IR-FSE) sequence, and T2-weighted magnetic resonance data may be collected by fast spin echo (FSE) sequence.

Figure 2:
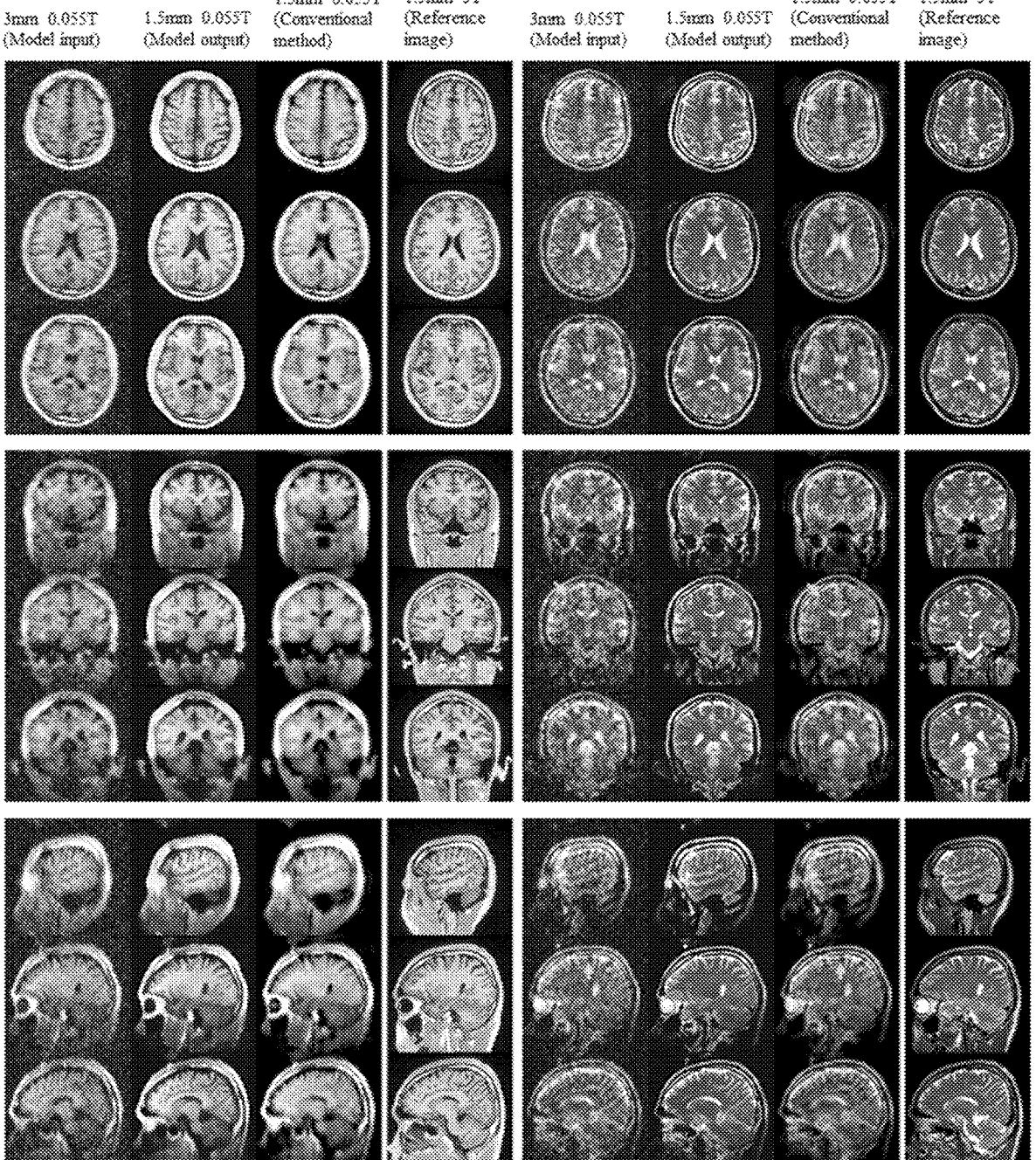
FIG. 2 is a comparison view between magnetic resonance images before and after reconstruction of image reconstruction model, reconstructed images obtained by conventional reconstruction methods and reference images in one or more embodiments in the present disclosure.

After collecting the down-sampled three-dimensional ultra-low field magnetic resonance data, the data processing module 2 may perform zero padding and Fourier transform on the down-sampled three-dimensional ultra-low field magnetic resonance data to obtain the three-dimensional isotropic ultra-low field magnetic resonance image, which is a 3 mm and 0.055 T magnetic resonance image, as shown in the first and fifth columns of FIG. 2.

The three-dimensional isotropic ultra-low field magnetic resonance image may be input into the pre-trained image enhancement model to obtain a fully sampled three-dimensional magnetic resonance enhanced image, as shown in the second and sixth columns in FIG. 2.

It can be seen that compared with reconstructed images obtained by a conventional Projections onto Convex Sets (POCS) reconstruction method shown in the third and seventh columns in FIG. 2, the ultra-low field magnetic resonance imaging system provided in the present disclosure significantly improves an image resolution and a signal-to-noise ratio, and significantly reduces image artifacts, as shown by arrows in the fifth and seventh columns in FIG. 2. An image quality of the fully-sampled three-dimensional magnetic resonance enhanced images in the present disclosure is similar to a reference images quality (such as the fourth and eighth columns in FIG. 2) collected by Signa EXCITE 3.0 T (GE 3 T) system. In addition, the present disclosure greatly reduces a scanning time, it allows rapidly ultra-low field magnetic resonance imaging with great quality.

In an embodiment, the ultra-low field magnetic resonance imaging system may further include a model training module 4, which is connected to the image enhancement module 3, and the model training module 4 may further include: a first processing unit 41, a second processing unit 42, and a training unit 43, the first processing unit 41 is configured for acquiring a plurality of full-sampled three-dimensional magnetic resonance images, and performing K-space clipping on each of the full-sampled three-dimensional magnetic resonance enhanced image to obtain a three-dimensional isotropic magnetic resonance image with first image quality;

the second processing unit 42 is connected to the first processing unit, and is configured for adding noise to the three-dimensional isotropic magnetic resonance image, and then sequentially performing K-space clipping, Fourier down sampling, zero-padding and Fourier transform on the three-dimensional isotropic magnetic resonance image added with the noise to obtain a three-dimensional isotropic magnetic resonance image with second image quality; the first image quality is greater than the second image quality; and the training unit 43 is connected to the first processing unit and the second processing unit, respectively, and the training unit 43 is configured for taking the three-dimensional isotropic magnetic resonance image with the first image quality and the corresponding three-dimensional isotropic magnetic resonance image with the second image quality as a training image pair to train and obtain the pre-trained image enhancement model.

Specifically, in the present embodiment, the full-sampled three-dimensional magnetic resonance images can be collected from a Human Connectome Project (HCP) public data set, and the noise added to the three-dimensional isotropic magnetic resonance image can include Rayleigh noise. During model training, the three-dimensional isotropic magnetic resonance image with the second image quality may be used as model input with a low resolution, a low signal-to-noise ratio and artifacts, and the three-dimensional isotropic magnetic resonance image with the first image quality may include a 3 mm and 3 T magnetic resonance image with great quality used as model output, so that a trained image enhancement model can enhance a low-quality three-dimensional isotropic magnetic resonance image into a great-quality three-dimensional isotropic magnetic resonance image.

Figure 3:
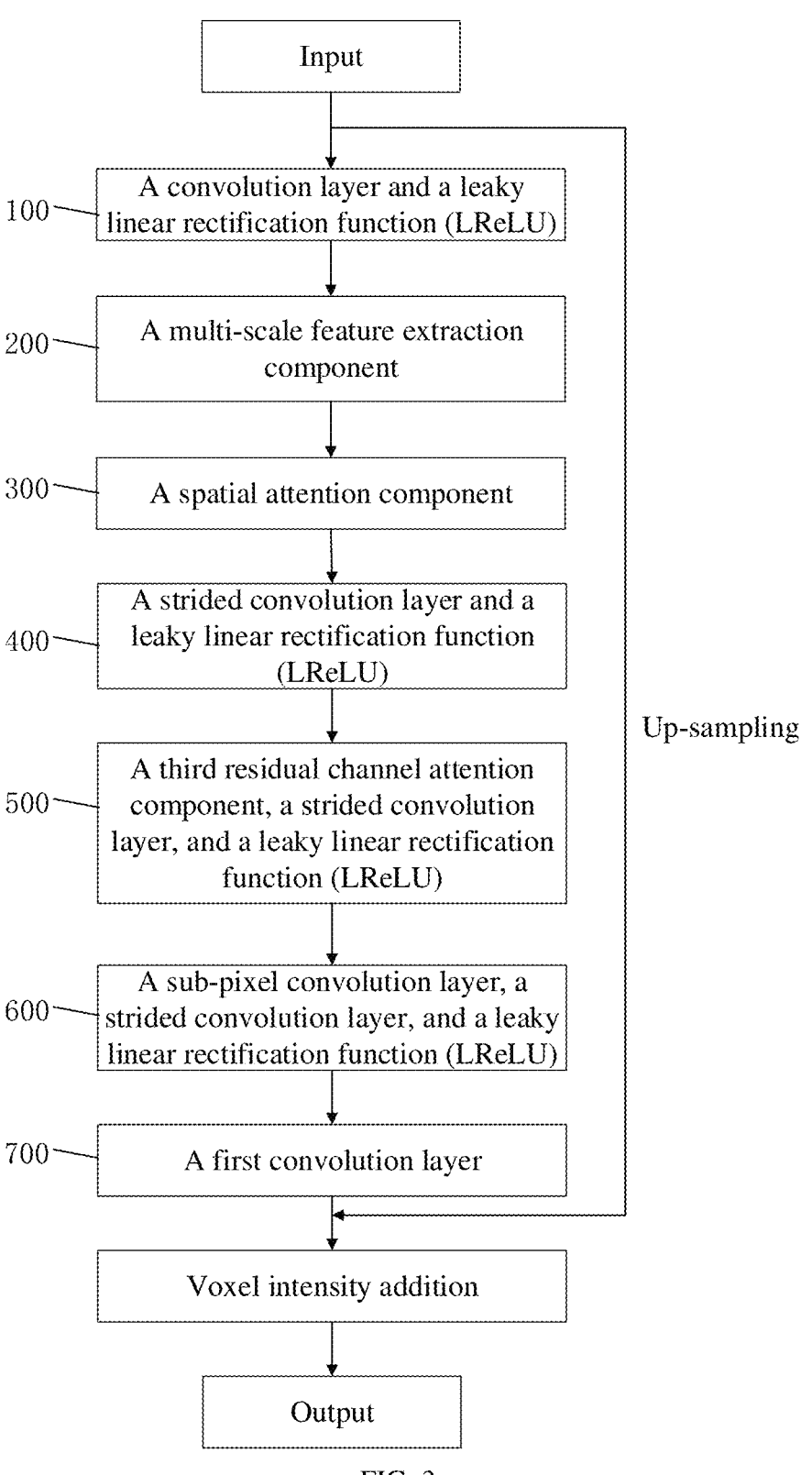
FIG. 3 is a schematic view of an overall network structure of an image enhancement model in one or more embodiments in the present disclosure.

In an embodiment, referring to FIG. 3, a network structure of the pre-trained image enhancement model may include a first convolution component 100, a multi-scale feature extraction component 200, a spatial attention component 300, a second convolution component 400, a first channel attention convolution component 500, a sub-pixel convolution component 600, and a first convolution layer 700;

an input of the first convolution component 100 is an input of the image enhancement model, and an output of the first convolution component 100 is connected to an input of a multi-scale feature extraction component 200;

an input of the spatial attention component 300 is connected to an output of the multi-scale feature extraction component 200, and an output of the spatial attention component 300 is connected to an input of the second convolution component 400;

an input of the first channel attention convolution component 500 is connected to an output of the second convolution component 400, and an output of the first channel attention convolution component 500 is connected to an input of the sub-pixel convolution component 600; and an input of the first convolution layer 700 is connected to an output of the sub-pixel convolution component 600, and voxel intensity of the input of the image enhancement model after up-sampling and voxel intensity of an output of the first convolution layer 700 are added to serve as an output of the image enhancement model.

Specifically, in the present embodiment, the first convolution module 100 may include a convolution layer and a leaky linear rectification function (LReLU), which are connected in sequence. The second convolution module 400 may include a strided convolution layer and a leaky linear rectification function (LReLU), which are connected in sequence. The sub-pixel convolution component 600 may include a sub-pixel convolution layer, a strided convolution layer, and a leaky linear rectification function (LReLU), which are connected in sequence. The multi-scale feature extraction component 200 is configured to extract local features on a top scale and semi-global features on a middle and lower scale. The spatial attention component 300 is configured to utilize a spatial relationship by modulating the features extracted by the multi-scale feature extraction component 200, and then features may be up-sampled into a great-resolution space by the sub-pixel convolution component, the up-sampled features may be converted into a three-dimensional image residual by the first convolution layer 700, and the final three-dimensional great-quality image may be obtained by adding the three-dimensional image residual with voxels of the three-dimensional low-quality image by interpolation up-sampling.

Figure 4:
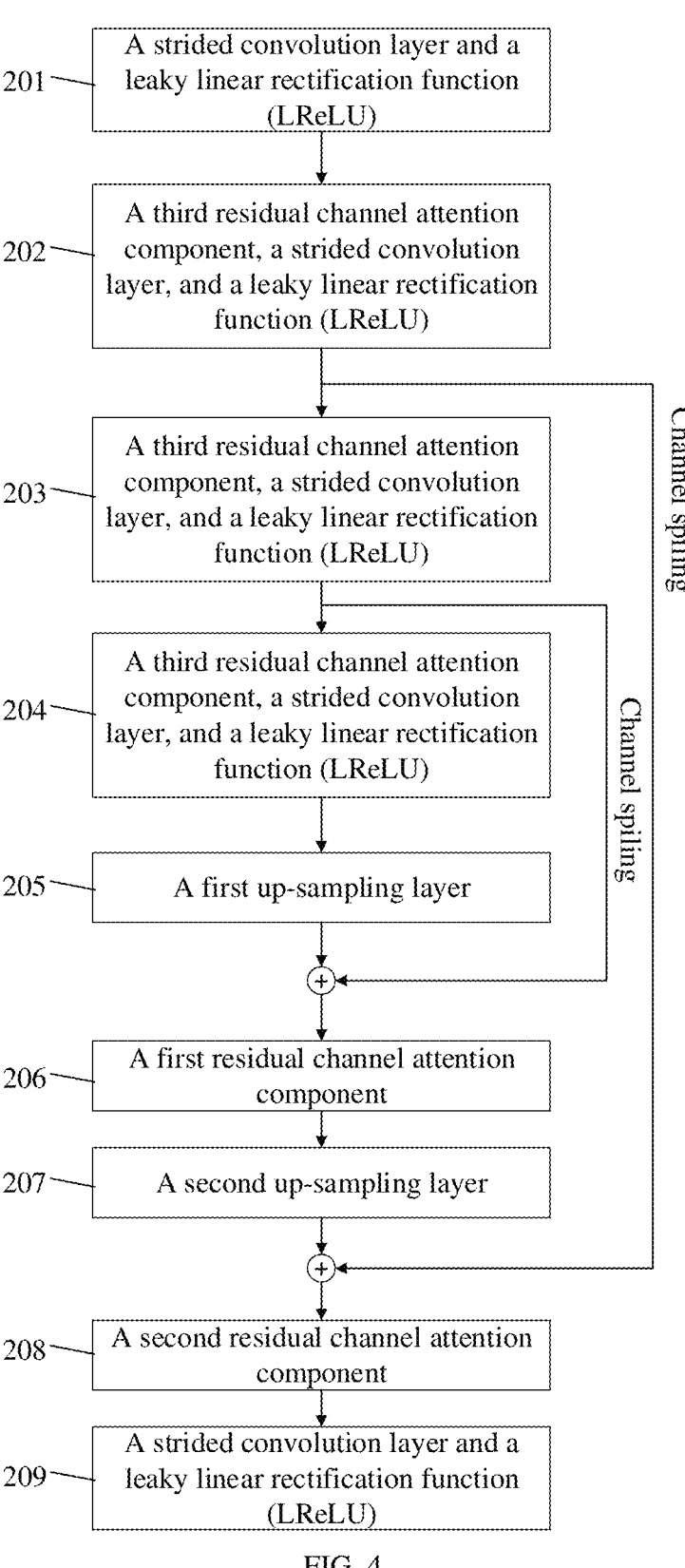
FIG. 4 is a schematic view of a network structure of a multi-scale feature extraction component in one or more embodiments in the present disclosure.

In an embodiment, referring to FIG. 4, the multi-scale feature extraction component 200 may include a first stride convolution component 201, a second channel attention convolution component 202, a third channel attention convolution component 203, a fourth channel attention convolution component 204, a first up-sampling layer 205, a first residual channel attention component 206, a second up-sampling layer 207, a second residual channel attention component 208, a second stride convolution component 209, an input of the first stride convolution component 201 is connected to the output of the first convolution component 100, and an output of the first stride convolution component 201 is connected to an input of the second channel attention convolution component 202;

an input of the third channel attention convolution component 203 is connected to an output of the second channel attention convolution component 202, and an output of the third channel attention convolution component 203 is connected to an input of the fourth channel attention convolution component 204;

an input of the first up-sampling layer 205 is connected to an output of the fourth channel attention convolution component 204, and an output of the first up-sampling layer 205 and the output of the third channel attention convolution component 203 are connected to an input of the first residual channel attention component 206 after channel splicing;

an input of the second up-sampling layer 207 is connected to an output of the first residual channel attention component 206, and an output of the second up-sampling layer 207 and the output of the second channel attention convolution component 202 are connected to an input of the second residual channel attention component 208 after channel splicing; and an input of the second stride convolution component 209 is connected to an output of the second residual channel attention component 208, and an output of the second stride convolution component 209 is connected to the input of the spatial attention component 300.

Specifically, the first stride convolution component 201 and the second stride convolution component 209 may both include a strided convolution layer and a leaky linear rectification function (LReLU), which are connected in sequence.

In an embodiment, the first channel attention convolution component 500, the second channel attention convolution component 202, the third channel attention convolution component 203, and the fourth channel attention convolution component 204 may all include a third residual channel attention component, a strided convolution layer, and a leaky linear rectification function (LReLU) which are connected in sequence.

Figure 5:
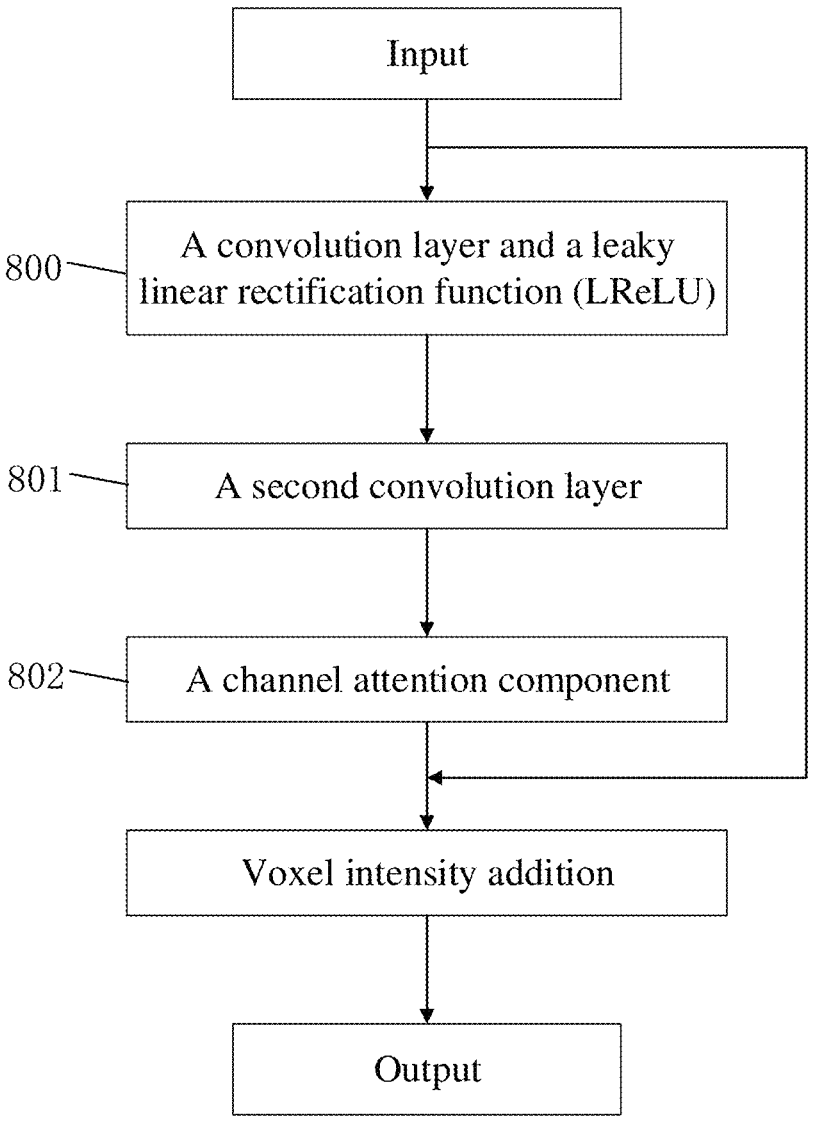
FIG. 5 is a schematic view of a network structure of a first residual channel attention component, a second residual channel attention component, and a third residual channel attention component.

In an embodiment, referring to FIG. 5, the first residual channel attention component 206, the second residual channel attention component 208, and the third residual channel attention component may all include a third convolution component 800, a second convolution layer 801, and a channel attention component 802 connected in sequence. Voxel intensity of an input of the third convolution component 800 and voxel intensity of an output of the channel attention component 802 may be added to serve as an output of the first residual channel attention component 206, an output of the second residual channel attention component 208, or an output of the third residual channel attention component.

Specifically, in the present embodiment, the third convolution component 800 may include a convolution layer and a leaky linear rectification function (LReLU) which are connected in sequence. In an embodiment, all the above convolution layers may be three-dimensional convolution layers, and a size of a convolution kernel of the three-dimensional convolution layers may be 3*3*3. The number of channels of all the above convolution layers may be 64, except that the number of channels of the convolution layers in the first convolution layer 100 is equal to the number of image groups, and the number of channels in the first convolution layer 700 may be 1. The loss function used in the present disclosure may be Structural Similarity (SSIM).

Referring to FIG. 6, the present disclosure further provides an ultra-low field magnetic resonance imaging method, which is applied to the above ultra-low field magnetic resonance imaging system, including:

step 1, the ultra-low field magnetic resonance imaging system collecting a down-sampled three-dimensional ultra-low field magnetic resonance data;

step 2, the ultra-low field magnetic resonance imaging system processing a three-dimensional ultra-low field magnetic resonance data to obtain a three-dimensional isotropic ultra-low field magnetic resonance image; and step 3, the ultra-low field magnetic resonance imaging system inputting the three-dimensional isotropic ultra-low field magnetic resonance image into a pre-trained image enhancement model to obtain a full-sampled three-dimensional magnetic resonance enhanced image.

Referring to FIG. 7, before step 1 is executed, the ultra-low field magnetic resonance imaging method may further include a model training process, and the model training process includes following steps:

step A1, the ultra-low field magnetic resonance imaging system acquiring a plurality of full-sampled three-dimensional magnetic resonance images, and performs K-space clipping on each full-sampled three-dimensional magnetic resonance image to obtain a three-dimensional isotropic magnetic resonance image with first image quality;

step A2, the ultra-low field magnetic resonance imaging system adding noise to the three-dimensional isotropic magnetic resonance image, and then sequentially performing K-space clipping, Fourier down sampling, zero padding and Fourier transform on the three-dimensional isotropic magnetic resonance image added with noise to obtain a three-dimensional isotropic magnetic resonance image with a second image quality; the first image quality is greater than the second image quality; and step A3, the ultra-low field magnetic resonance imaging system taking the three-dimensional isotropic magnetic resonance image with the first image quality and the corresponding three-dimensional isotropic magnetic resonance image with the second image quality as training image pairs to train and obtain the pre-trained image enhancement model.

Specific limitations on the method may be referred to the above limitations on the system, which will not be repeated herein. The foregoing modules and units may be implemented by using a general computing apparatus. The modules and units may be concentrated on a single computing apparatus or distributed on a network formed by multiple computing apparatuses. Alternatively, the modules and units may be implemented by using program code executable by the computing apparatus. Therefore, the modules and units may be stored in the storage apparatus and executed by the computing apparatus. In some cases, the modules and units may be separately fabricated into integrated circuit modules, or multiple modules in the modules may be fabricated into a single integrated circuit module. This application is not limited to any specific hardware and software combination.

The various technical features of the above-described embodiments may be combined arbitrarily, and all possible combinations of the various technical features of the above-described embodiments have not been described for the sake of conciseness of description. However, as long as there is no contradiction in the combinations of these technical features, they should be considered to be within the scope of the present specification.

The above-described embodiments express only several embodiments of the present disclosure, which are described in a more specific and detailed manner, but are not to be construed as a limitation on the scope of the present disclosure. For one skilled in the art, several deformations and improvements can be made without departing from the conception of the present disclosure, all of which fall within the scope of protection of the present disclosure. Therefore, the scope of protection of the present disclosure shall be subject to the attached claims.

What is claimed is:

1. An ultra-low field magnetic resonance imaging system, comprising:

means for collecting a down-sampled three-dimensional ultra-low field magnetic resonance data;

means for processing a three-dimensional ultra-low field magnetic resonance data to obtain a three-dimensional isotropic ultra-low field magnetic resonance image; and means for processing data, for inputting the three-dimensional isotropic ultra-low field magnetic resonance image into a pre-trained image enhancement model to obtain a full-sampled three-dimensional magnetic resonance enhanced image.

2. The ultra-low field magnetic resonance imaging system of claim 1, wherein the down-sampled three-dimensional ultra-low field magnetic resonance data comprises K-space data with Fourier down sampling along two dimensions, wherein T1-weighted magnetic resonance data is collected by inversion recovery fast spin echo sequence, and T2-weighted magnetic resonance data is collected by fast spin echo sequence.

3. The ultra-low field magnetic resonance imaging system of claim 1, wherein processing the three-dimensional ultra-low field magnetic resonance data comprises performing zero-padding and Fourier transform on the three-dimensional ultra-low field magnetic resonance data to obtain the three-dimensional isotropic ultra-low field magnetic resonance image.

4. The ultra-low field magnetic resonance imaging system of claim 1, further comprising:

means for acquiring a plurality of full-sampled three-dimensional magnetic resonance images, and performing K-space clipping on each of the full-sampled three-dimensional magnetic resonance enhanced image to obtain a three-dimensional isotropic magnetic resonance image with first image quality;

means for adding noise to the three-dimensional isotropic magnetic resonance image, and then sequentially performing K-space clipping, Fourier down sampling, zero-padding and Fourier transform on the three-dimensional isotropic magnetic resonance image added with the noise to obtain a three-dimensional isotropic magnetic resonance image with second image quality, wherein the first image quality is greater than the second image quality; and means for taking the three-dimensional isotropic magnetic resonance image with the first image quality and the corresponding three-dimensional isotropic magnetic resonance image with the second image quality as a training image pair to train and obtain the pre-trained image enhancement model.

5. The ultra-low field magnetic resonance imaging system of claim 1, wherein a network structure of the pre-trained image enhancement model comprises a first convolution component, a multi-scale feature extraction component, a spatial attention component, a second convolution component, a first channel attention convolution component, a sub-pixel convolution component, and a first convolution layer, an input of the first convolution component is an input of the image enhancement model, and an output of the first convolution component is connected to an input of a multi-scale feature extraction component;

an input of the spatial attention component is connected to an output of the multi-scale feature extraction component, and an output of the spatial attention component is connected to an input of the second convolution component;

an input of the first channel attention convolution component is connected to an output of the second convolution component, and an output of the first channel attention convolution component is connected to an input of the sub-pixel convolution component; and an input of the first convolution layer is connected to an output of the sub-pixel convolution component, and voxel intensity of the input of the image enhancement model after up-sampling and voxel intensity of an output of the first convolution layer are added to serve as an output of the image enhancement model.

6. The ultra-low field magnetic resonance imaging system of claim 5, wherein the multi-scale feature extraction component comprises a first stride convolution component, a second channel attention convolution component, a third channel attention convolution component, a fourth channel attention convolution component, a first up-sampling layer, a first residual channel attention component, a second up-sampling layer, a second residual channel attention component, a second stride convolution component, an input of the first stride convolution component is connected to the output of the first convolution component, and an output of the first stride convolution component is connected to an input of the second channel attention convolution component;

an input of the third channel attention convolution component is connected to an output of the second channel attention convolution component, and an output of the third channel attention convolution component is connected to an input of the fourth channel attention convolution component;

an input of the first up-sampling layer is connected to an output of the fourth channel attention convolution component, and an output of the first up-sampling layer and the output of the third channel attention convolution component are connected to an input of the first residual channel attention component after channel splicing;

an input of the second up-sampling layer is connected to an output of the first residual channel attention component, and an output of the second up-sampling layer and the output of the second channel attention convolution component are connected to an input of the second residual channel attention component after channel splicing; and an input of the second stride convolution component is connected to an output of the second residual channel attention component, and an output of the second stride convolution component is connected to the input of the spatial attention component.

7. The ultra-low field magnetic resonance imaging system of claim 6, wherein the first channel attention convolution component, the second channel attention convolution component, the third channel attention convolution component, ponent, the third channel attention convolution component, and the fourth channel attention convolution component all comprise a third residual channel attention component, a strided convolution layer, and a linear rectification function with leakage which are connected in sequence.

8. The ultra-low field magnetic resonance imaging system of claim 7, wherein the first residual channel attention component, the second residual channel attention component, and the third residual channel attention component all comprise a third convolution component, a second convolution layer, and a channel attention component connected in sequence, and voxel intensity of an input of the third convolution component and voxel intensity of an output of the channel attention component are added to serve as an output of the first residual channel attention component, an output of the second residual channel attention component, or an output of the third residual channel attention component.

9. An ultra-low field magnetic resonance imaging method, which is applied to the ultra-low field magnetic resonance imaging system of claim 1, comprising:

step 1, the ultra-low field magnetic resonance imaging system collecting a down-sampled three-dimensional ultra-low field magnetic resonance data;

step 2, the ultra-low field magnetic resonance imaging system processing a three-dimensional ultra-low field magnetic resonance data to obtain a three-dimensional isotropic ultra-low field magnetic resonance image; and step 3, the ultra-low field magnetic resonance imaging system inputting the three-dimensional isotropic ultra-low field magnetic resonance image into a pre-trained image enhancement model to obtain a full-sampled three-dimensional magnetic resonance enhanced image.

10. The ultra-low field magnetic resonance imaging method of claim 9, wherein before step 1 is executed, the ultra-low field magnetic resonance imaging method further comprises a model training process, and the model training process comprises following steps:

step A1, the ultra-low field magnetic resonance imaging system acquiring a plurality of full-sampled three-dimensional magnetic resonance images, and performs K-space clipping on each full-sampled three-dimensional magnetic resonance image to obtain a three-dimensional isotropic magnetic resonance image with first image quality;

step A2, the ultra-low field magnetic resonance imaging system adding noise to the three-dimensional isotropic magnetic resonance image, and then sequentially performing K-space clipping, Fourier down sampling, zero padding and Fourier transform on the three-dimensional isotropic magnetic resonance image added with noise to obtain a three-dimensional isotropic magnetic resonance image with a second image quality, wherein the first image quality is greater than the second image quality; and step A3, the ultra-low field magnetic resonance imaging system taking the three-dimensional isotropic magnetic resonance image with the first image quality and the corresponding three-dimensional isotropic magnetic resonance image with the second image quality as training image pairs to train and obtain the pre-trained image enhancement model.

* * * * *